United States Patent [19]
Thomas

[11] Patent Number: 5,988,170
[45] Date of Patent: Nov. 23, 1999

[54] SNORING PREVENTION APPARATUS

[76] Inventor: Thomas Thomas, 1110 Breezy Meadow La., Spencer, Iowa 51301

[21] Appl. No.: 08/861,675

[22] Filed: May 22, 1997

[51] Int. Cl.[6] ........................................................ A61F 5/56
[52] U.S. Cl. ............................ 128/848; 128/860; 602/902
[58] Field of Search ............................ 128/848, 859–862; 602/902

[56] References Cited

U.S. PATENT DOCUMENTS

| | | | |
|---|---|---|---|
| 2,669,988 | 2/1954 | Carpenter | 128/861 |
| 2,882,893 | 4/1959 | Godfroy | 128/861 |
| 4,270,531 | 6/1981 | Blachly | 128/861 |
| 4,676,240 | 6/1987 | Gardy | 128/207.14 |
| 4,971,072 | 11/1990 | Randall | 128/857 |
| 5,533,523 | 7/1996 | Bass | 128/859 |

*Primary Examiner*—Michael A. Brown
*Attorney, Agent, or Firm*—Merchant & Gould P.C.

[57] ABSTRACT

A snoring prevention apparatus for depressing a person's tongue during sleep is provided which includes a base plate, a tongue depressing member, an opening through which air may flow and a flexible band or strap to secure the apparatus to the person's mouth. The tongue depressing member is preferably a substantially flat member that extends from the base plate for disposition against the upper surface of the tongue such that the person's tongue is depressed which opens the airway of the person and prevents snoring. The flexible band is connected to the base plate and is disposed against the person's head for maintaining the apparatus in place. The tongue depressing member is resilient and flexible between a first tongue depressing position and a second upper position such that the tongue depressing member flexes from the first position to the second position in response to a normal body function which requires the tongue to raise during sleep, such as swallowing, coughing or sneezing. After the body function is accommodated, the tongue depressing member flexes back to the first tongue depressing position.

11 Claims, 5 Drawing Sheets

SNORING PREVENTION APPARATUS

BACKGROUND OF THE INVENTION

1. Field of the Invention

This invention relates generally to the field of snoring prevention devices. This invention relates more particularly to depressing the tongue as a means for treating snoring.

2. Description of the Art

Snoring is a condition that occurs during sleep when inhaled or exhaled air vibrates the soft palate, uvula and adjacent structures, thereby causing a loud noise. In extreme cases it can cause sleep apnea, a temporary cessation of breathing during sleep. A number of devices are known in the prior art to address the problem of snoring. Unfortunately, these devices have significant drawbacks in terms of comfort, durability, reliability and effectiveness.

U.S. Pat. No. 5,046,512 to Murchie discloses an apparatus for treating snoring by regulating the air flow into the person's mouth. Unfortunately this device must be held by a person's teeth and can easily fall out of the mouth in the middle of the night. Also, in the event the person needs to swallow, cough or sneeze in the middle of the night the device will be dislodged from its functional location.

A device disclosed in U.S. Pat. No. 1,674,336 to King addresses the problem of snoring by providing an aperture to ensure a clear breathing path at the mouth. It also slightly separates the maxillary jaw from the mandibular jaw in order to create more space in the back of the throat for air to travel through. Unfortunately this device also must be held by the teeth and can become easily dislodged during sleep by a cough or sneeze.

U.S. Pat. Nos. 5,092,346 and 5,277,272 to Hays et al. and Hays, respectively, disclose a device which, when properly held in place with the teeth, projects the mandibular jaw slightly forward. This brings the back of the tongue forward such that the gap between the soft palette and the back of the tongue is enlarged to allow a more clear airway. The Hays devices have several drawbacks. First, they must be custom-fitted to the teeth of the individual. This custom-fitting, along with any necessary adjustments, requires the time and cost of professional services. Also, such a device can still become dislodged by a cough or sneeze, without returning to its functional position.

It is also known in the art to treat snoring by pulling the tongue forward as in U.S. Pat. No. 5,465,734 to Alvarez et al. This device contains an annular constricted sleeve portion using a suction force to pull the tongue forward and a mouth shield for positioning of the device. This device suffers from numerous drawbacks. Because the tongue is not free to rise, this device does not allow for swallowing, coughing or sneezing. If the person requires such a normal body function, the tongue will pull itself out from the annular sleeve portion, breaking the suction seal, thereby rendering the device nonfunctional. Further, the device is uncomfortable for the person.

It is also known in the art to suspend the soft palette while simultaneously depressing the tongue in an anti-snoring device disclosed in U.S. Pat. No. 3,132,647 to Corniello. This device resides completely inside the mouth. However, this device must be custom fitted to each individual person because of the method with which it attaches to the maxillary jaw. Also, if this device comes loose in the middle of the night it loses its functionality and could cause an obstruction to normal breathing. Finally, the presence of this device exerting an upward force on the uvula and soft palate is extremely uncomfortable and could cause gagging.

What is needed is an apparatus that will prevent snoring by depressing the tongue while ensuring that the apparatus does not become dislodged in the middle of the night. Further, what is needed is an apparatus that will allow the tongue to be raised temporarily for the purpose of swallowing, coughing or sneezing with the apparatus returning to its functional position immediately thereafter. It is further desired to provide an apparatus that prevents "lip-popping", another sleeping ailment whereby the force of expelled air pops open the closed lips causing an annoying noise. Further, the apparatus must be comfortable to wear and appropriate for use during sleep.

SUMMARY OF THE INVENTION

The present invention provides a snoring prevention apparatus for depressing the tongue to provide an open breathing passageway to prevent snoring. The invention effectively prevents snoring while allowing normal body functions by the user including swallowing, coughing and sneezing and also breathing through the mouth.

According to one aspect of the present invention, there is provided a snoring prevention apparatus including a base plate and a tongue depressing member extending from the base plate into a person's mouth. The base plate includes an opening to permit airflow therethrough. The tongue depressing member exerts a downward force against the upper surface of the tongue to depress the tongue and provide an open breathing passageway.

Pursuant to one embodiment, the tongue depressing member is resilient and flexible so that the tongue depressing member flexes between a first tongue depressing position and a second upper position. The tongue depressing member is sufficiently resilient so that the tongue depressing member is permitted to flex upward in response to a normal body function, after which the tongue depressing member flexes back to its functional position due to the resilient nature of the tongue depressing member. In this way, when a person must swallow, cough or sneeze, the tongue will rise, thereby pressing up against the tongue depressing member and causing the tongue depressing member to flex upward. After the body function is completed, the tongue depressing member will flex back to its normal functional position to depress the tongue when the tongue is in its relaxed state.

Preferably, a flexible band or strap is connected to the base plate and disposed around the person's head. The flexible strap is designed to maintain the base plate against the person's mouth so that the tongue depressing member can depress the person's tongue when the tongue is in its relaxed state. Preferably, the flexible strap or band is sufficiently resilient so that the base plate of the apparatus may be pushed away from the person's face and allow a greater opening to facilitate a normal body function by the wearer such as swallowing, coughing or sneezing.

Preferably, the apparatus includes a clip connected to the flexible strap or band for adjusting the force applied by the strap to the base plate. This adjusting mechanism ensures a comfortable fit as well as maintaining the apparatus in its functional position.

Pursuant to one embodiment, the tongue depressing member is substantially flat to promote a comfortable engagement with the tongue and the opening in the base plate is formed as a cutout portion adjacent the connection of the tongue depressing member and base plate. This allows for comfortable depression of the tongue while still permitting mouth breathing by the user.

The present invention has numerous advantages over the prior art. It allows both mouth breathing and nasal breathing throughout the night. The tongue depressant member is of sufficient size and in the necessary location to prevent "lip-popping." It need not be fitted to the individual person, unlike many of the prior known inventions. It is usable while lying on one's side or back or stomach, unlike previous inventions which will fall out, be dislodged, or no longer be in their functional positions based on the positioning of the person. It avoids contact with the upper and soft palettes, thereby providing an added element of comfort. Also, it can be made of soft material which is comfortable for the surrounding teeth and gums of the person.

The above-mentioned features and advantages, along with various other advantages and features of novelty, are pointed out with particularity in the claims of the present application which form a part hereof. However, for a better understanding of the invention, its advantages, and objects obtained by its use, reference should be made to the drawings which form a further part of the present application and to the accompanying descriptive manner in which there is illustrated and described preferred embodiments of the invention.

DETAILED DESCRIPTION OF THE PREFERRED EMBODIMENT

Figure 1A:
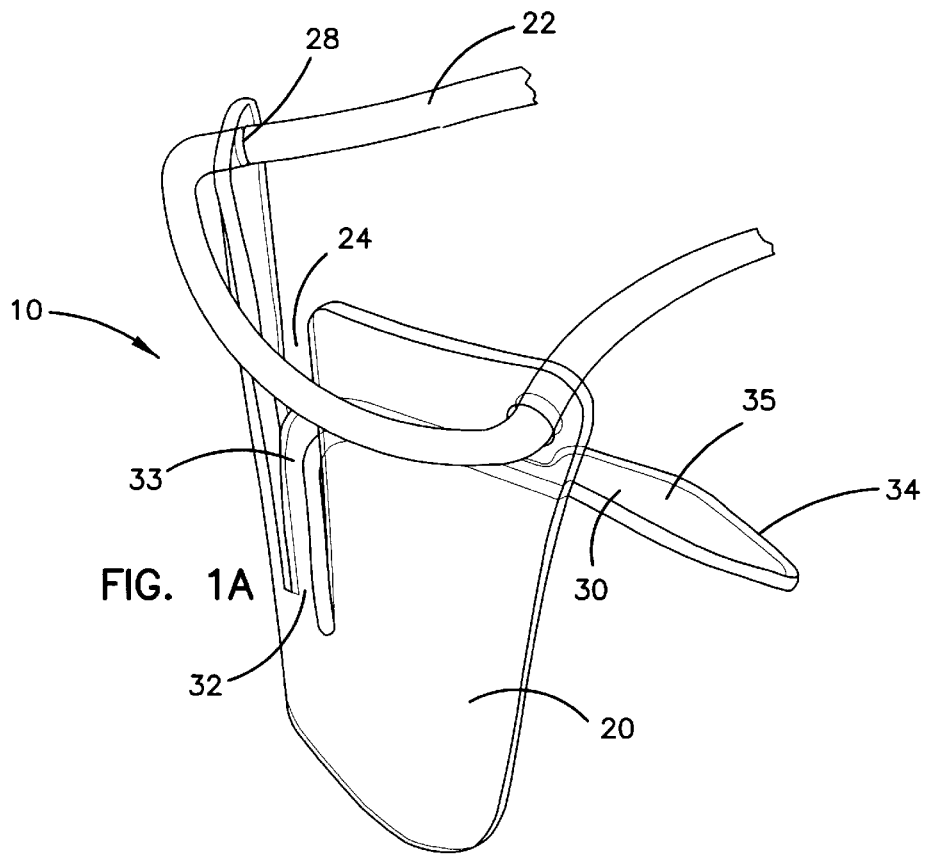
FIG. 1A is a perspective view of a snoring prevention apparatus according to the principles of the present invention.
Figure 1B:
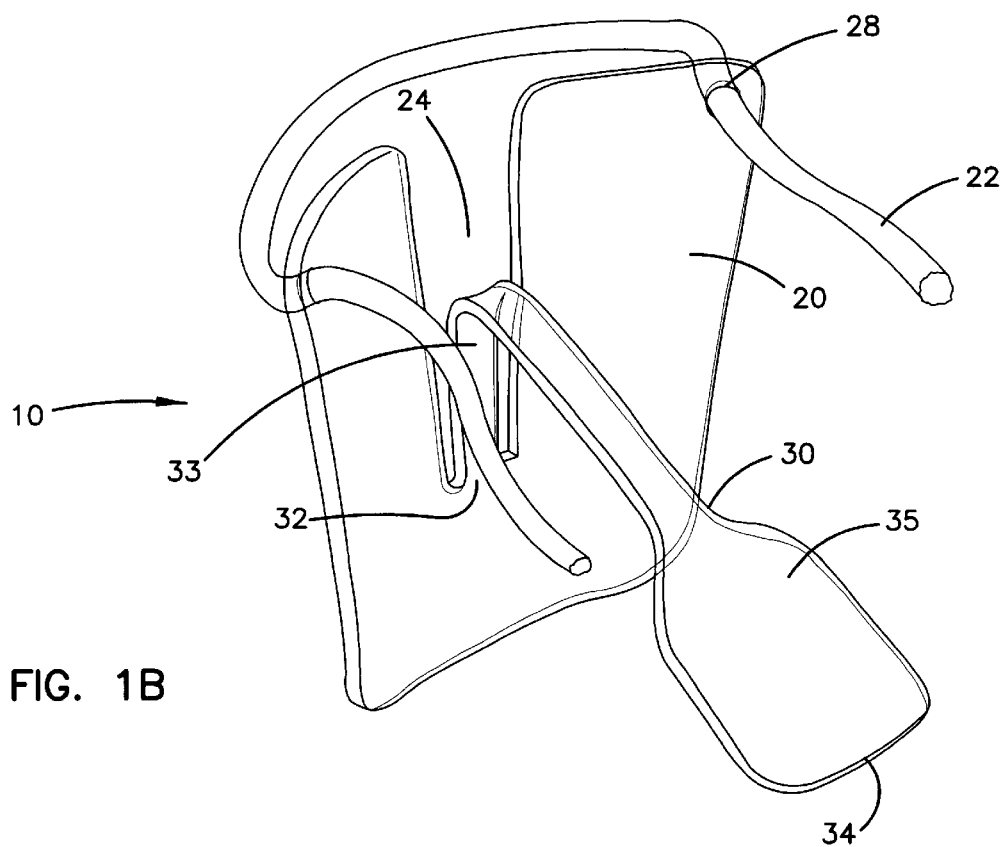
FIG. 1B is a perspective view of a snoring prevention apparatus according to the principles of the present invention.
Figure 4:
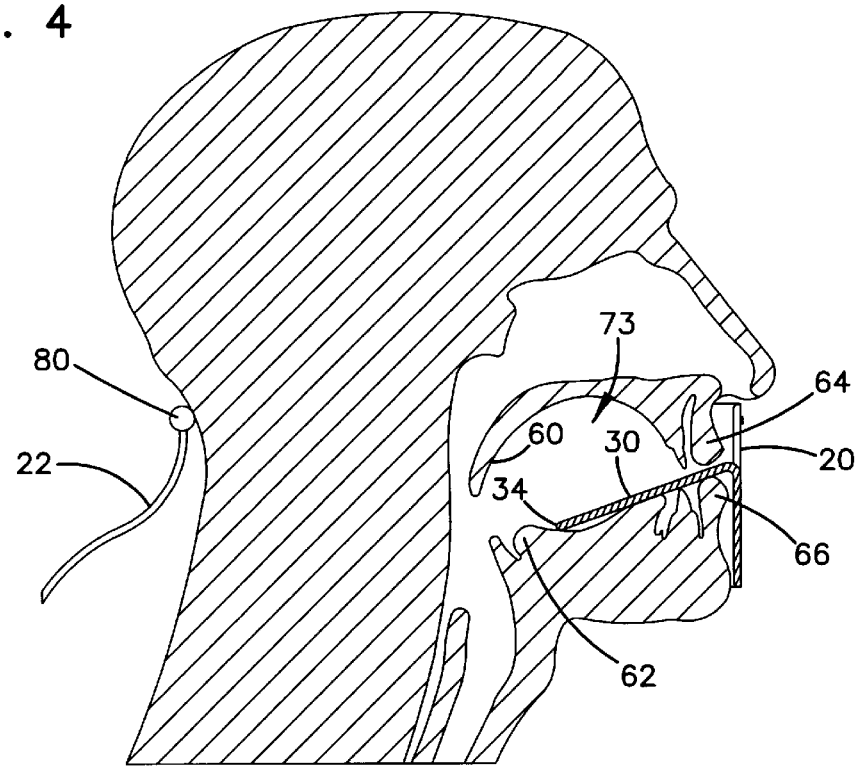
FIG. 4 is a side-sectional view of a snoring prevention apparatus according to the principles of the present invention disposed in its functional position in the mouth of a person showing depression of the tongue and subsequent opening of the person's airway.
Figure 5:
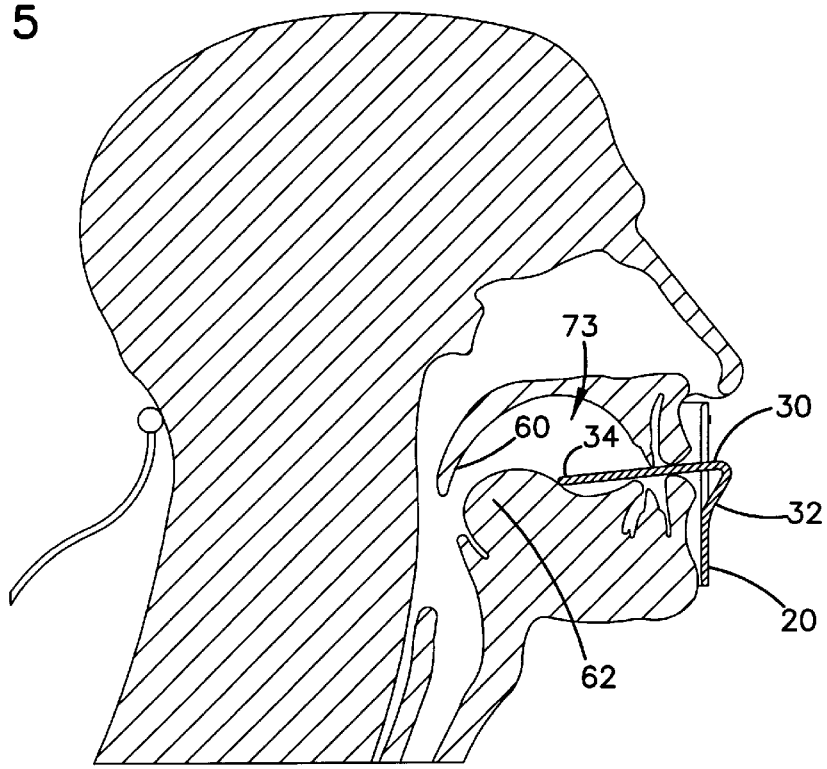
FIG. 5 is a side-sectional view of the apparatus shown in FIG. 4 showing the person performing a normal body function with the tongue rising in response to said function, causing the tongue depressing member to flex.

Referring now to the drawings, in which similar elements are numbered identically throughout, a description of preferred embodiments is provided. In FIGS. 1A–1B, a perspective view of a snoring prevention apparatus according to the principles of the present invention is generally illustrated at 10 and includes a base plate 20. The base plate 20 may be substantially curved to fit comfortably around the person's mouth as shown in FIGS. 4 and 5. FIGS. 4 and 5 show the base plate 20 fitting around a person's mouth and making contact with upper lip 64 and lower lip 66 of the user. The base plate 20 is preferably made of a rigid, yet soft, plastic which is slightly malleable such that it may conform somewhat to the person's lips, yet rigid enough to maintain its general shape as illustrated in FIG. 1A. It is appreciated that many types of plastic or other suitable materials may be used for the base plate 20 in the present invention.

The base plate 20 has an opening 24 to permit airflow therethrough. This allows a person to breath through the mouth while using the invention. In the embodiment shown in FIGS. 1–3, the opening 24 is formed as a cutout portion in the center of the base plate 20 adjacent the tongue depressing member 30. According to another embodiment shown in FIGS. 6–7, the opening 24 is formed as an aperture located substantially in the center of the base plate 20 and is large enough to allow one to breathe easily therethrough. It is noted that the size and location of the opening on the base plate may be varied while still allowing the invention to accomplish its functional purposes. The opening 24 permits a person to utilize both mouth and nasal breathing during sleep.

Figure 2:
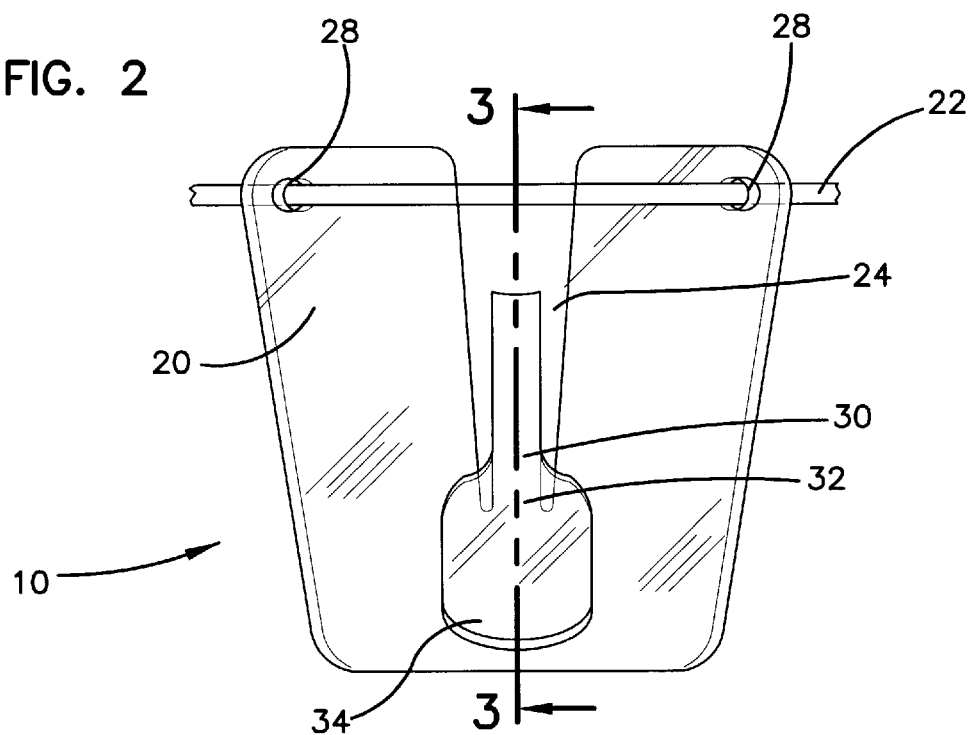
FIG. 2 is a front view of the snoring prevention apparatus shown in FIG. 1A.
Figure 3:
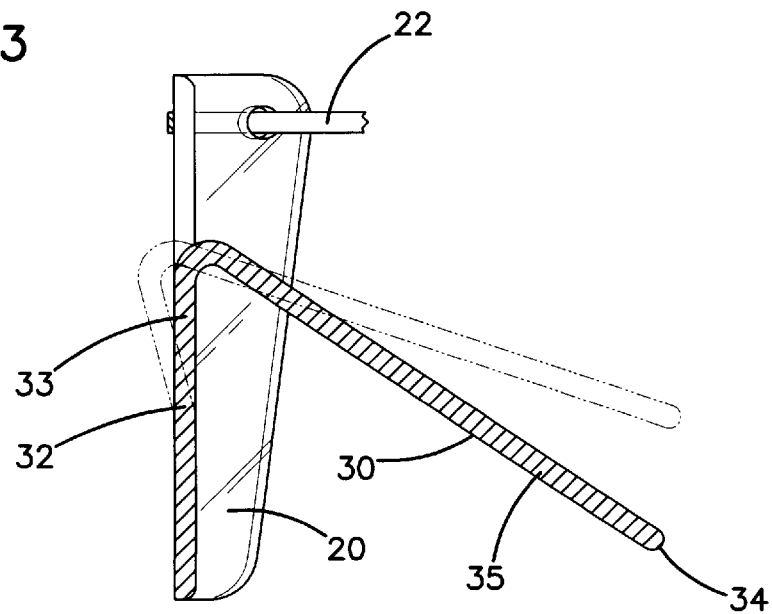
FIG. 3 is a side sectional view of the snoring prevention apparatus shown in FIG. 1A.

Referring now to FIGS. 1–3, a flexible tongue depressing member 30 having a first end 32 and a second end 34 is connected to the base plate 20 and extends therefrom, preferably at a slight downward angle. The tongue depressing member 30 is formed from a resilient material so that it is flexible between a normal, tongue depressing position and a raised position. As shown in FIG. 3, the tongue depressing member 30 is permitted to flex between a lower, normal position and a raised position (shown in phantom).

According to one embodiment, the tongue depressing member 30 has a first portion 33 which extends upward from the base plate 20 and a second portion 35 which extends at a downward angle from the first portion 33. In this way, the tongue depressing member 30 is permitted to flex both upward and forward with respect to the base plate 20 as shown in FIG. 3. Accordingly, this helps prevent the tongue depressing member 30 from contacting the soft palette of the person during use.

Figure 6:
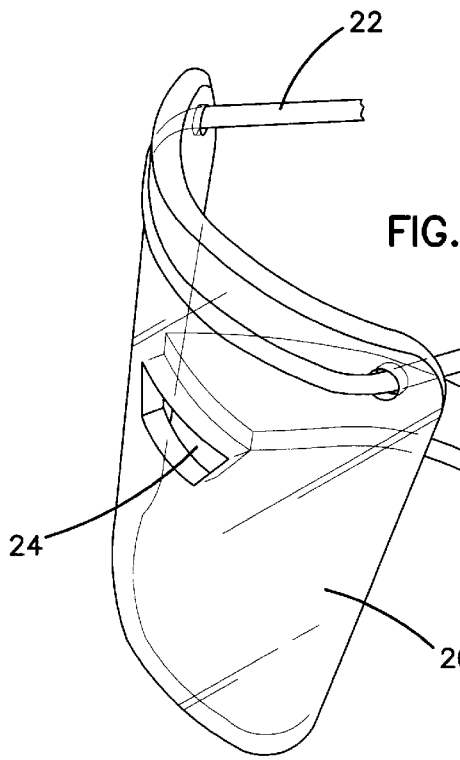
FIG. 6 is a perspective view of an alternative embodiment of the present invention.
Figure 7:
FIG. 7 is a side sectional view of the alternate embodiment shown in FIG. 6.
Figure 8:
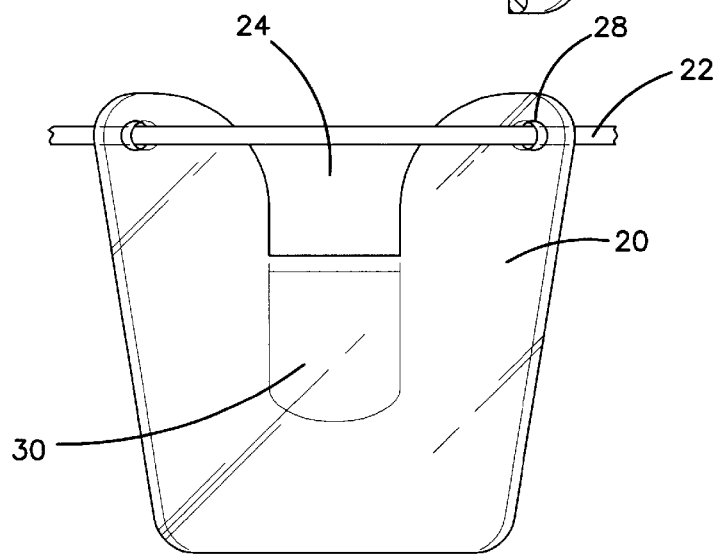
FIG. 8 is a front view of a second alternative embodiment of the present invention showing the opening in the base plate formed as a cutout portion above the tongue depressing member.

In this embodiment, the opening 24 is formed in the center of base plate 20 adjacent the first portion 33 of the tongue depressing member 30. Referring to FIGS. 6–8, alternative embodiments are illustrated in which in the tongue depressing member 30 is shown with different shapes. Also, the opening 24 may be fashioned as an aperture disposed beneath the connection of the tongue depressing member 30 and the base plate 20 as shown in FIGS. 6–7. Alternatively, the opening 24 may be designed as a cutout portion above the connection of the tongue depressing member 30 and base plate 20 as shown in FIG. 8. It is appreciated that the tongue depressing member may be formed in a variety of shapes and still perform its function of depressing the tongue and retaining its flexible nature.

It is appreciated that the tongue depressing member 30 is designed for placement against the person's tongue. (See FIGS. 4 and 5). The tongue depressing member 30 is sufficiently resilient to exert a force against the tongue so that the tongue is depressed. When the tongue 62 is depressed, the opening in the person's throat between the soft palette 60 and the back of the tongue 62 is increased, thereby allowing unobstructed airflow up and down the throat and, ultimately, preventing snoring (See FIG. 4).

The tongue depressing member 30 may be composed of the same material as the base plate 20, though the base plate 20 and tongue depressing member 30 need not necessarily be composed of the same material. In one embodiment, the tongue depressing member 30 is made of a material commercially known as LEXAN or U-VEX. It is appreciated that various other materials may be utilized to provide a flexible, resilient tongue depressing member 30. It is noted that the location of the tongue depressing member 30 with respect to the person's upper lip 64 and lower lip 66 is such that "lip-popping" is prevented by providing an obstacle to the lip seal required for lip-popping. If the lips cannot seal, they cannot "pop" open.

Referring to FIGS. 1A–1B, a flexible band or strap 22 is provided for connection to the base plate 20. This connection may be accomplished by numerous methods such as stringing the strap 22 through apertures 28, in the base plate 20. The flexible band or strap 22 is preferably constructed of an elastic material such that the band 22 can stretch and then return to its previous position. As shown in FIG. 2, the band 22 is preferably disposed against the base plate 20. Pursuant to this embodiment, the elastic band 22 is utilized to maintain the base plate 20 in position against the person's face so that the tongue depressing member 30 is positioned to depress the person's tongue. Referring to FIG. 4, the elastic band 22 is disposed around and contacts the person's head 68. The band 22 applies a force directly to the base plate 20 to hold the base plate 20 against the person's upper lip 64 and lower lip 66 to keep the apparatus firmly and comfortably in place on the person's face.

Although an elastic band 22 is illustrated here, it is appreciated that numerous other methods for maintaining the position of the apparatus may be used in accordance with the principles of the present invention. For example, a string with sufficient flexibility could be utilized in place of the elastic band. Alternatively, the band 22 can be attached at various locations to the base plate 20 and could be adapted to be secured to different parts of person's head, such as the ears.

From the foregoing, it is apparent that this invention need not be specially fit to each individual person, unlike many of the devices in the prior art. It is further apparent that the elastic band 22 allows the apparatus to be functional even while lying on one's side, back or stomach, or when the mouth is slightly opened in the middle of the night, unlike previous inventions which will fall out, be dislodged or no longer be in their functional positions based on the positioning of the person.

Referring now to FIGS. 4 and 5, the snoring prevention apparatus 10 is shown disposed in its functional position in the mouth 73 of a person showing depression of the tongue 62 by the tongue depressing member 30 and subsequent opening of the person's airway, defined as the space between the soft palate 60 and the back of the tongue 62. In FIG. 5 the person is shown performing a normal body function and the tongue depressing member 30 is displaced from its functional position to allow the person to perform the body function. FIGS. 4 and 5 together illustrate one aspect of the present invention: the ability for the person to conduct normal body functions, such as swallowing, coughing or sneezing while wearing the apparatus. The body functions herein referred to include any function wherein the tongue 62 must rise in order for the function to proceed properly and to its completion.

FIG. 5 shows the tongue 62 rising in response to said function, thereby exerting a force at the contact point between the tongue 62 and second end 34 of the tongue depressing member 30. This force causes the tongue depressing member 30 to flex upward (FIG. 5). In this position, shown in FIG. 5, the person may expel any extra air, fluids or solids that need be expelled in order to properly perform the body function. The air pathway between the person's mouth 73 and the apparatus opening 24 allows for said expulsion. Once the body function is complete, the tongue depressing member 30 flexes back to its normal position to depress the person's tongue 62 (FIG. 4) and prevent snoring. Thus, the apparatus 10 allows a person to sleep comfortably while preventing snoring but still permitting the user to perform normal body functions.

According to one embodiment as illustrated in FIGS. 4–5, the tongue depressing member 30 may preferably be designed to flex both upward and forward with respect to the base plate 20. In this way, the second end 34 of the tongue depressing member 30 moves upward and outward with respect to the person's mouth when the person is performing a normal body function in which the tongue must rise. In this way, the second end 34 of the tongue depressing member 30 moves forward so as not to contact the soft palette 60 at the back of the person's mouth. This prevents the tongue depressing member 30 from irritating the back of the person's mouth when the person performs a normal body function during sleep and results in added comfort during use.

In a preferred embodiment, it is appreciated that the flexible nature of the elastic band 22 is such that the base plate 20 may be permitted to pivot outward (away from) the person's mouth in conjunction with the flexing of the tongue depressing member 30 in response to a body function of a person. In this way, the second end 34 of the tongue depressing member 30 moves further away from the soft palette 60 of the person to prevent contact with the back of the person's mouth during a normal body function.

It is appreciated that the flexible fit of the elastic band 22, the conformity of the base plate 20 to the person's mouth, the use of soft, yet rigid, plastic and the lack of contact with the upper and soft palettes of the user all provide an added element of comfort to the user.

Pursuant to another aspect of a preferred embodiment, a clip 80 is attached to the elastic band 26 for adjusting the force applied by the band 26 to the base plate 20. In this way the apparatus is adjustable to comfortably fit a user's head even with variations in the size of the user's head. It will be appreciated that the clip 80 shown here is one of numerous clipping devices available and any one of these devices will function with the present invention. Alternatively, the elastic band may be simply tied at the back of the person's head.

Figure 9:
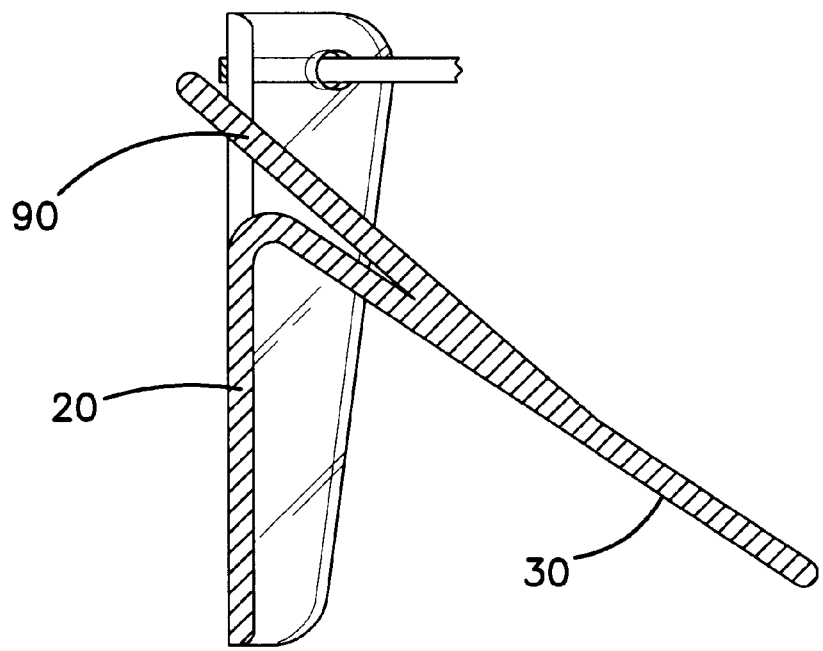
FIG. 9 is a side sectional view of a third alternative embodiment of the present invention.

Referring to FIG. 9, another embodiment is illustrated in which the apparatus 10 preferably includes a flange member 90 which extends upward from the tongue depressing member 30 through the opening 24 in the base plate 20. The flange member 90 is preferably formed integral with the tongue depressing member 30 and is flexible for added comfort to the user. In practice, the flange member 90 serves to maintain the person's mouth in a slightly open position during use so that the person is better able to breathe through the mouth. In this way, the flange member 90 helps eliminate "nasal" snoring since the person is permitted to breathe through the mouth which reduces the amount of air entering and exiting through the nose.

It is to be understood that even though numerous characteristics and advantages of various embodiments of the present invention have been set forth in the foregoing description, together with the details of the structure and function of the various embodiments of the invention, this disclosure is illustrative only and changes may be made in the detail, especially in matters of shape, size and arrangement of parts with the principles of the present invention, to the full extent indicated by the broad general meaning of the terms in which the appended claims are expressed.

Other modifications of the invention will be apparent to those skilled in the art in view of the foregoing descriptions. These descriptions are intended to provide specific examples of embodiments which clearly disclose the present invention. Accordingly, the invention is not limited to the described embodiments or to the use of limited to the described embodiments or to the use of specific elements, dimensions, materials or configurations contained therein. All alternative modifications and variations of the present invention which fall within the spirit and broad scope of the appended claims are covered.

What is claimed is:

1. A snoring prevention apparatus for insertion in a person's mouth to depress the person's tongue, comprising:

a base plate for disposition against the person's mouth and having an opening to permit air flow therethrough, the base plate including a lower member extending downward from the opening and terminating at a lower end such that a portion of the lower member of the base plate is disposed against the person's chin;

a tongue depressing member connected to said base plate for extension from said base plate into the mouth of the person for disposition against a portion of the person's tongue to depress the tongue; and a flexible band connected to the base plate for placement around the person's head such that the base plate is maintained in a first position against the person's mouth whereby the tongue depressing member exerts a force on the person's tongue sufficient to depress the tongue;

wherein in response to a normal body function of the person, the lower portion of the base plate acts as a pivot point against the person's chin such that the base plate pivots outward away from the mouth of the person to permit upward movement of the tongue against the tongue depressing member after which the flexible band exerts a force on base plate to return the base plate to the first position.

2. The apparatus according to claim 1 wherein a portion of the tongue depressing member extends at a downward angle from the base plate such that the tongue depressing member is adapted to flex upward and outward with respect to the person's mouth in response to a normal body function of the person.

3. The apparatus according to claim 1 further comprising a clip connected to the flexible band for adjusting the force applied by the band to the base plate.

4. The apparatus according to claim 1 wherein said tongue depressing member is substantially flat and said opening in the base plate is positioned adjacent the connection of the tongue depressing member and base plate.

5. The apparatus according to claim 1 further comprising a flange member connected to the tongue depressing member and extending upward through the opening in the base plate such that the flange member and tongue depressing member together maintain the person's mouth in a partially open position.

6. The apparatus of claim 1 wherein the tongue depressing member is resilient and flexible between a first tongue depressing position and a second upper position such that the tongue depressing member flexes from the first position to the second position in response to a normal body function of the person to permit upward movement of the tongue after which the tongue depressing member flexes back to the first tongue depressing position.

7. A snoring prevention apparatus for insertion in a person's mouth to depress the person's tongue, comprising:

a base plate for disposition against the person's mouth;

a tongue depressing member connected to said base plate for extension from said base plate into the mouth of the person for disposition against a portion of the person's tongue to depress the tongue, the tongue depressing member including a first portion adjacent the base plate and a second portion terminating at an end opposite the base plate, the first portion having a narrower width than the second portion of the tongue depressing member;

wherein the tongue depressing member is resilient and flexible between a first tongue depressing position and a second position such that the tongue depressing member flexes upward with respect to the person's mouth from the first position to the second position in response to a normal body function of the person after which the tongue depressing member flexes back to the first position to depress the tongue.

8. The apparatus of claim 7 wherein the base plate includes an opening to permit airflow therethrough.

9. A snoring prevention apparatus for insertion in a person's mouth to depress the person's tongue, comprising:

a base plate for disposition against the person's mouth and having an opening to permit air flow therethrough, the base plate including a lower member extending downward from the opening and terminating at a lower end such that a portion of the lower member of the base plate is disposed against the person's chin;

a tongue depressing member connected to said base plate for extension from said base plate into the mouth of the person for disposition against a portion of the person's tongue to depress the tongue, said tongue depressing member flexible between a first tongue depressing position and a second upper position; and a flexible band connected to the base plate wherein the band exerts a force to maintain the base plate against the person's mouth wherein in response to a normal body function of the person, the lower portion of the base plate acts as a pivot point against the person's chin such that the base plate pivots outward away from the mouth of the person to permit upward movement of the tongue against the tongue depressing member after which the flexible band exerts a force on base plate to return the base plate to position against the person's mouth.

10. The apparatus of claim 9 wherein said tongue depressing member is substantially flat and said opening in the base plate is positioned adjacent the connection of the tongue depressing member and base plate.

11. The apparatus according to claim 9 wherein a portion of the tongue depressing member extends at a downward angle from the base plate such that the tongue depressing member is adapted to flex upward and outward with respect to the person's mouth in response to a normal body function of the person.

* * * * *